United States Patent
Tyler et al.

(10) Patent No.: US 11,116,977 B2
(45) Date of Patent: Sep. 14, 2021

(54) SYSTEMS AND METHODS FOR CONTROLLING LEVELS OF PERCEIVED INTENSITY OF A SENSORY STIMULUS

(71) Applicants: Case Western Reserve University, Cleveland, OH (US); The University of Chicago, Chicago, IL (US)

(72) Inventors: Dustin James Tyler, Cleveland, OH (US); Emily Lauren Graczyk, Cleveland, OH (US); Sliman Julien Bensmaia, Chicago, IL (US); Benoit Pierre Delhaye, Cleveland, OH (US); Hannes Philipp Saal, Cleveland, OH (US)

(73) Assignees: CASE WESTERN RESERVE UNIVERSITY, Cleveland, OH (US); THE UNIVERSITY OF CHICAGO, Chicago, IL (US)

( * ) Notice: Subject to any disclaimer, the term of this patent is extended or adjusted under 35 U.S.C. 154(b) by 199 days.

(21) Appl. No.: 16/341,084

(22) PCT Filed: Oct. 11, 2017

(86) PCT No.: PCT/US2017/056070
§ 371 (c)(1),
(2) Date: Apr. 11, 2019

(87) PCT Pub. No.: WO2018/071494
PCT Pub. Date: Apr. 19, 2018

(65) Prior Publication Data
US 2020/0230416 A1     Jul. 23, 2020

Related U.S. Application Data

(60) Provisional application No. 62/407,202, filed on Oct. 12, 2016, provisional application No. 62/537,992, filed on Jul. 28, 2017.

(51) Int. Cl.
*A61N 1/36* (2006.01)
*A61N 1/05* (2006.01)

(52) U.S. Cl.
CPC ....... *A61N 1/36103* (2013.01); *A61N 1/0553* (2013.01); *A61N 1/0556* (2013.01);
(Continued)

(58) Field of Classification Search
CPC ............ A61N 1/36103; A61N 1/36031; A61N 1/36034; A61N 1/0553; A61N 1/0556;
(Continued)

(56) References Cited

U.S. PATENT DOCUMENTS

2015/0328465 A1* 11/2015 Tyler .................. A61N 1/36031
607/62

FOREIGN PATENT DOCUMENTS

WO     2015/095092 A1    6/2015

OTHER PUBLICATIONS

Anani, A. B., K. Ikeda, and L. M. Körner. "Human ability to discriminate various parameters in afferent electrical nerve stimulation with particular reference to prostheses sensory feedback." Medical and Biological Engineering and Computing 15.4 (1977): 363-373.
(Continued)

Primary Examiner — Lindsey G Wehrheim
(74) Attorney, Agent, or Firm — Tarolli, Sundheim, Covell & Tummino LLP

(57) ABSTRACT

One aspect of the present disclosure relates to a method for controlling levels of perceived intensity of a sensory stimulus. The method includes configuring a stimulation signal with an activation charge rate (ACR) based on a predefined level of intensity by a subject during an action. The ACR is based on a strength of pulses in the stimulation signal parameter and a frequency of pulses in the stimulation signal
(Continued)

parameter. The stimulation signal can be applied to neural tissue of a subject during the action. Based on the stimulation signal, the subject can be induced to perceive the predefined level of intensity during the action.

17 Claims, 11 Drawing Sheets

(52) U.S. Cl.
CPC ....... *A61N 1/3615* (2013.01); *A61N 1/36031* (2017.08); *A61N 1/36034* (2017.08); *A61N 1/36132* (2013.01); *A61N 1/36192* (2013.01); *A61N 1/36196* (2013.01)

(58) Field of Classification Search
CPC .............. A61N 1/36132; A61N 1/3615; A61N 1/36192; A61N 1/36196
See application file for complete search history.

(56) References Cited

OTHER PUBLICATIONS

Bensmaia, Sliman J. "Tactile intensity and population codes." Behavioural brain research 190.2 (2008): 165-173.
Bensmaia, Sliman J., et al. "Vibratory adaptation of cutaneous mechanoreceptive afferents." Journal of neurophysiology 94.5 (2005): 3023-3036.
Brill, Natalie, and Dustin Tyler. "Optimizing nerve cuff stimulation of targeted regions through use of genetic algorithms." 2011 Annual International Conference of the IEEE Engineering in Medicine and Biology Society. IEEE, 2011.
Burgess, P. R., et al. "The neural signal for skin indentation depth. I. Changing indentations." Journal of Neuroscience 3.8 (1983): 1572-1585.
Clark, Gregory A., et al. "Using multiple high-count electrode arrays in human median and ulnar nerves to restore sensorimotor function after previous transradial amputation of the hand." 2014 36th Annual International Conference of the IEEE Engineering in Medicine and Biology Society. IEEE, 2014.
Crago, Patrick E., P. Hunter Peckham, and Geoffrey B. Thrope. "Modulation of muscle force by recruitment during intramuscular stimulation." IEEE Transactions on Biomedical Engineering 12 (1980): 679-684.
Dhillon, Gurpreet Singh, and Kenneth W. Horch. "Direct neural sensory feedback and control of a prosthetic arm." IEEE transactions on neural systems and rehabilitation engineering 13.4 (2005): 468-472.
Dhillon, G. S., et al. "Effects of short-term training on sensory and motor function in severed nerves of long-term human amputees." Journal of neurophysiology 93.5 (2005): 2625-2633.
Gescheider, George A., and John H. Wright. "Effects of sensory adaptation on the form of the psychophysical magnitude function for cutaneous vibration." Journal of experimental psychology 77.2 (1968): 308.
Gorman, Peter H., and J. Thomas Mortimer. "The effect of stimulus parameters on the recruitment characteristics of direct nerve stimulation." IEEE Transactions on Biomedical Engineering 7 (1983): 407-414.
Gracyzk, Emily L., et al. "The neural basis of perceived intensity in natural and artificial touch." Science translational medicine 8.362 (2016): 362ra142-362ra142.
Grill, Warren M., and Cameron C. McIntyre. "Extracellular excitation of central neurons: implications for the mechanisms of deep brain stimulation." Thalamus & Related Systems 1.3 (2001): 269-277.
Hollins, Mark, et al. "Time course and action spectrum of vibrotactile adaptation." Somatosensory & motor research 7.2 (1990): 205-221.

Hollins, Sliman J. Bensmaïa, Sean Washburn, Mark. "Vibrotactile adaptation impairs discrimination of fine, but not coarse, textures." Somatosensory & motor research 18.4 (2001): 253-262.
Johansson, Roland S., and J. Randall Flanagan. "Coding and use of tactile signals from the fingertips in object manipulation tasks." Nature Reviews Neuroscience 10.5 (2009): 345.
Johnson, K. O. "Reconstruction of population response to a vibratory stimulus in quickly adapting mechanoreceptive afferent fiber population innervating glabrous skin of the monkey." Journal of Neurophysiology 37.1 (1974): 48-72.
Kaczmarek, Kurt A., et al. "Electrotactile and vibrotactile displays for sensory substitution systems." IEEE Transactions on Biomedical Engineering 38.1 (1991): 1-16.
Leung, Y. Y., et al. "Time-course of vibratory adaptation and recovery in cutaneous mechanoreceptive afferents." Journal of neurophysiology 94.5 (2005): 3037-3045.
Mcintyre, Cameron C., Andrew G. Richardson, and Warren M. Grill. "Modeling the excitability of mammalian nerve fibers: influence of afterpotentials on the recovery cycle." Journal of neurophysiology 87.2 (2002): 995-1006.
Mcintyre, Cameron C., and Warren M. Grill. "Finite element analysis of the current-density and electric field generated by metal microelectrodes." Annals of biomedical engineering 29.3 (2001): 227-235.
Mei, J., et al. "The neural signal for skin indentation depth. II. Steady indentations." Journal of Neuroscience 3.12 (1983): 2652-2659.
Menia, Lisa L., and Clayton L. Van Doren. "Independence of pitch and loudness of an electrocutaneous stimulus for sensory feedback." IEEE Transactions on Rehabilitation Engineering 2.4 (1994): 197-206.
Muniak, Michael A., et al. "The neural coding of stimulus intensity: linking the population response of mechanoreceptive afferents with psychophysical behavior." Journal of Neuroscience 27.43 (2007): 11687-11699.
Ochoa, José L. "Intraneural microstimulation in humans." Neuroscience letters 470.3 (2010): 162.
Ochoa, Jose, and Erik Torebjörk. "Sensations evoked by intraneural microstimulation of single mechanoreceptor units innervating the human hand." The Journal of physiology 342.1 (1983): 633-654.
PCT International Search Report and Written Opinion for corresponding International Application Serial No. PCT/US2017/056070, dated Feb. 5, 2018, pp. 1-17.
Peterson, E. J., O. Izad, and Dustin J. Tyler. "Predicting myelinated axon activation using spatial characteristics of the extracellular field." Journal of neural engineering 8.4 (2011): 046030.
Polasek, Katharine H., et al. "Stimulation stability and selectivity of chronically implanted multicontact nerve cuff electrodes in the human upper extremity." IEEE transactions on neural systems and rehabilitation engineering 17.5 (2009): 428-437.
Polasek, Katharine H., et al. "Human nerve stimulation thresholds and selectivity using a multi-contact nerve cuff electrode." IEEE transactions on neural systems and rehabilitation engineering 15.1 (2007): 76-82.
Poulos, Dennis A., et al. "The neural signal for the intensity of a tactile stimulus." Journal of Neuroscience 4.8 (1984): 2016-2024.
Raspopovic, Stanisa, et al. "Restoring natural sensory feedback in real-time bidirectional hand prostheses." Science translational medicine 6.222 (2014): 222ra19-222ra19.
Saal, Hannes P., and Sliman J. Bensmaia. "Biomimetic approaches to bionic touch through a peripheral nerve interface." Neuropsychologia 79 (2015): 344-353.
Schiefer, Matthew, et al. "Sensory feedback by peripheral nerve stimulation improves task performance in individuals with upper limb loss using a myoelectric prosthesis." Journal of neural engineering 13.1 (2015): 016001.
Stevens, Stanley Smith. "The direct estimation of sensory magnitudes: Loudness." The American journal of psychology 69.1 (1956): 1-25.
Swallow, M. I. C. H. A. E. L. "Fibre size and content of the anterior tibial nerve of the foot." Journal of neurology, neurosurgery, and psychiatry 29.3 (1966): 205.

(56) References Cited

OTHER PUBLICATIONS

Szeto, Andrew YJ, John Lyman, and Ronald E. Prior. "Electrocutaneous pulse rate and pulse width psychometric functions for sensory communications." Human Factors 21.2 (1979): 241-249.

Szeto, Andrew YJ, and Frank A. Saunders. "Electrocutaneous stimulation for sensory communication in rehabilitation engineering." IEEE Transactions on Biomedical Engineering 4 (1982): 300-308.

Szeto, Andrew YJ. "Relationship between pulse rate and pulse width for a constant-intensity level of electrocutaneous stimulation." Annals of biomedical engineering 13.5 (1985): 373-383.

Tabot, Gregg A., et al. "Restoring the sense of touch with a prosthetic hand through a brain interface." Proceedings of the National Academy of Sciences 110.45 (2013): 18279-18284.

Talbot, William H., et al. "The sense of flutter-vibration: comparison of the human capacity with response patterns of mechanoreceptive afferents from the monkey hand." Journal of neurophysiology 31.2 (1968): 301-334.

Tan, Daniel W., et al. "A neural interface provides long-term stable natural touch perception." Science translational medicine 6.257 (2014): 257ra138-257ra138.

Tan, Daniel W., et al. "Stability and selectivity of a chronic, multi-contact cuff electrode for sensory stimulation in human amputees." Journal of neural engineering 12.2 (2015): 026002.

Torebjork, H. E., W. Schady, and J. Ochoa. "Sensory correlates of somatic afferent fibre activation." Human neurobiology 3.1 (1984): 15-20.

Torebjork, H. E., Å. B. Vallbo, and J. L. Ochoa. "Intraneural microstimulation in man: Its relation to specificity of tactile sensations." Brain 110.6 (1987): 1509-1529.

Tyler, Dustin J. "Neural interfaces for somatosensory feedback: bringing life to a prosthesis." Current opinion in neurology 28.6 (2015): 574.

Tyler, Dustin J., and Dominique M. Durand. "Functionally selective peripheral nerve stimulation with a flat interface nerve electrode." IEEE Transactions on Neural Systems and Rehabilitation Engineering 10.4 (2002): 294-303.

Verdu, Enrique, et al. "Influence of aging on peripheral nerve function and regeneration." Journal of the Peripheral Nervous System 5.4 (2000): 191-208.

Wheat, Heather E., Lauren M. Salo, and Antony W. Goodwin. "Human ability to scale and discriminate forces typical of those occurring during grasp and manipulation." Journal of Neuroscience 24.13 (2004): 3394-3401.

Whitney, Alice G., et al. "The cutaneous contribution to adaptive precision grip." Trends in neurosciences 27.10 (2004): 637-643.

Yoshida, Ken, and Ken Horch. "Selective stimulation of peripheral nerve fibers using dual intrafascicular electrodes." IEEE transactions on biomedical engineering 40.5 (1993): 492-494.

* cited by examiner

SYSTEMS AND METHODS FOR CONTROLLING LEVELS OF PERCEIVED INTENSITY OF A SENSORY STIMULUS

CROSS-REFERENCE TO RELATED APPLICATIONS

This application claims the benefit of U.S. Provisional Application No. 62/537,992, entitled "SYSTEMS AND METHODS FOR CONTROLLING LEVELS OF PERCEIVED INTENSITY OF A SENSORY STIMULUS," filed 28 Jul. 2017. This application also claims the benefit of U.S. Provisional Application No. 62/407,202, entitled "THE NEURAL BASIS OF PERCEIVED INTENSITY IN NATURAL AND ARTIFICIAL TOUCH," filed 12 Oct. 2016. The entirety of these provisional applications is hereby incorporated by reference for all purposes.

TECHNICAL FIELD

The present disclosure relates generally to sensory perception and, more specifically, to systems and methods for controlling levels of perceived intensity of a sensory stimulus.

BACKGROUND

Sensation refers to detection of external or internal stimulation by receptors in a subject's body. The detected stimulation can be transduced into an electrical signal, which is then transmitted to the brain. Within the brain, the sensation conveyed in the electrical signal can be perceived. In other words, perception utilizes the brain to make sense of the stimulation. In some instances, a subject may be unable to detect such external or internal stimulation. For example, the subject may be suffering from paralysis or amputation may be unable to experience such sensations. Sensation can be restored to these subjects through electrical stimulation of sensory nerves, where electrical signals can be transmitted to the brain so that the subject can perceive the sensation without communication from the receptors. While modifications to parameters of the electrical waveform, such as changing the pulse frequency or changing the charge per pulse (by manipulating pulse amplitude or pulse width) are known to affect perception, it remains unknown how to control a level of intensity that is provided through a peripheral nerve interface.

SUMMARY

The present disclosure relates generally to sensory perception and, more specifically, to systems and methods for controlling levels of perceived intensity of a sensory stimulus. The levels of perceived intensity can be controlled based on an activation charge rate (ACR), a stimulation parameter that combines the pulse frequency and the charge per pulse to approximate the total spike rate evoked in the activated neuronal population.

In one aspect, the present disclosure can include a system for controlling levels of perceived level of intensity to be perceived based on a sensory stimulus. The system can include at least one electrode (e.g., an implanted electrode). The system can also include a controller comprising a processor to configure a stimulation signal with an ACR based on a predefined intensity of sensory perception by a subject during an action. The ACR can include a strength of pulses in the stimulation signal parameter and a frequency of pulses in the stimulation signal parameter. The system can also include a waveform generator to generate the stimulation signal and provide the stimulation signal to the electrode for application to the subject as an action is performed. The at least one electrode can be configured to apply the stimulation signal to the subject as the action is performed.

In another aspect, the present disclosure can include a method for controlling levels of perceived intensity of a sensory stimulation. The method can include configuring, by a system comprising a processor (e.g., a controller), a stimulation signal with an ACR set based on a predefined level of intensity to be perceived by a subject during an action. The ACR comprises a strength of pulses in the stimulation signal parameter and a frequency of pulses in the stimulation signal parameter. The method can also include applying, by a neural prosthesis device coupled to the system, the stimulation signal to neural tissue of a subject during the action. The method can also include inducing the subject to perceive the level of intensity during the action based on the stimulation signal and the predefined intensity of sensory perception.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
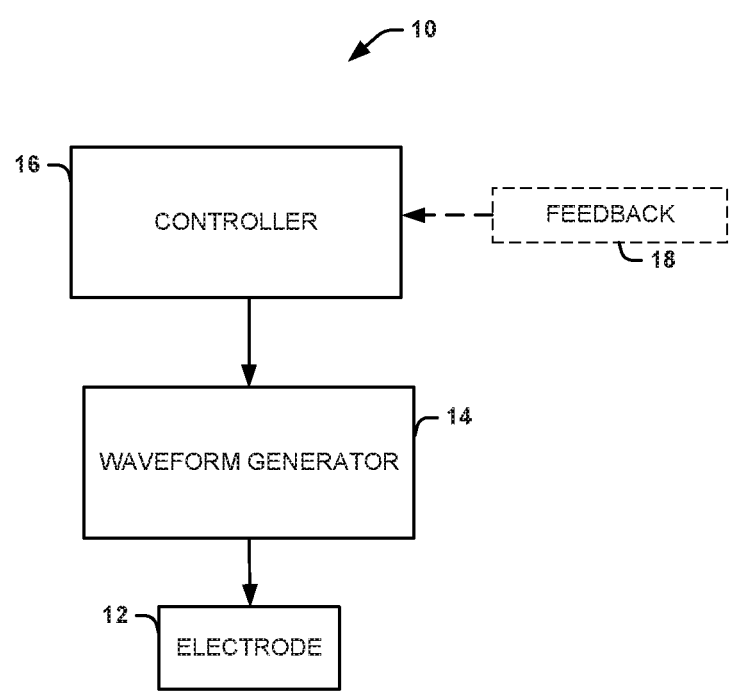
FIG. 1 is a block diagram illustration showing an example of a system that controls levels of perceived intensity of a sensory stimulus in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "sensory nervous system" can refer to a part of the nervous system responsible for processing sensory information. The sensory nervous system includes sensory receptors involved in sensation, sensory nerves and neural pathways, and parts of the brain involved in sensory perception.

As used herein, the term "sensation" can refer to detection of external or internal stimulation (otherwise known as a sensory stimulus) by sensory receptors. Upon detection, the stimulation can be transduced into an electrical signal, which is transmitted to the brain through one or more sensory nerves and/or neural pathways.

As used herein, the term "artificial" sensation can refer to an electrical signal that is applied to one or more sensory nerves through one or more electrodes of a neural prosthesis and transmitted to the brain. The artificial sensation can be used to restore sensation in instances where a subject is unable to detect external or internal stimulation, such as due to amputation or paralysis.

As used herein, the term "perception" can refer to the act of one or more parts of the brain processing the electrical signal to determine the sensed stimulation. Perception can be used to determine a level of intensity of a sensation during an action. For example, a subject can perceive differences between a strong handshake and a bone-crushing grasp.

As used herein, the term "neural prosthesis" can refer to a series of devices that can substitute a modality that may have been damaged as a result of an injury or a disease or enhance a modality that has not been damaged. The modality can be motor, sensory, and/or cognitive. The neural prosthesis described herein substitutes at least the sensory modality.

As used herein, the term "adaptation" can refer to a change over time of the responsiveness of the sensory nervous system to a stimulus.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "real time" can be used to refer to the processing of input data within milliseconds so to be available virtually immediately as feedback.

II. Overview

The present disclosure relates generally to sensory perception, the act of one or more parts of a subject's brain processing the electrical signal to determine a level of intensity sensation during an action. The sensory nervous system includes sensory receptors involved in sensation, sensory nerves and neural pathways, and parts of the brain involved in sensory perception. Sometimes, however, a subject is in need of artificial sensation that bypasses the sensory receptors and relies on electrical stimulation of one or more sensory nerves For example, the subject may be suffering from a disease, paralysis, or amputation, which can disrupt sensation and/or perception. As another example, the subject may be entirely healthy, but emerged in a virtual reality-type environment where physical stimulation may or may not directly exist except in mathematical expressions. For example, the data can be from a physics domain, such as ultrasound or other imaging modality.

Generally, electrical stimulation of one or more sensory nerves (e.g., by a neural prosthesis) can provide a degree of sensory perception; however, electrical stimulation alone cannot inform the subject as to the level of intensity of the sensation. As an example, electrical stimulation can alert a subject of a hand grasp, but cannot allow the subject to distinguish whether the hand grasp is a firm handshake or a bone crushing grip without visual cues and learned behavior. The present disclosure relates, more specifically, to systems and methods for controlling levels of perceived intensity of a sensory stimulus. The levels of perceived intensity can be controlled based on a single parameter of the electrical stimulation, the activation charge rate (ACR). For example, the ACR can be updated in real time based on an input (e.g., feedback from a sensor, based on a predefined program, or other types of feedback). The ACR approximates the total spike rate evoked in the activated neural population and combines the pulse frequency and the charge per pulse. As such, by controlling the ACR of an electrical stimulation, a desired level of perceived intensity can be perceived for a desired action.

III. Systems

One aspect of the present disclosure can include a system 10 (FIG. 1) for controlling levels of perceived intensity of a sensory stimulus by a subject. The levels can be controlled and updated in real time based on feedback (e.g., from a sensor, based on an input, based on a predefined program, based on an input from an image, or the like). The system 10 can be used by a subject to perceive a level of intensity of a certain sensory stimulus based on an action taken by the subject or done onto the subject. The subject can be, for example, an able-bodied individual, an ill individual, an amputee, and/or a paralyzed individual. In an example, the system 10 can be used in connection with a prosthetic limb to replace missing sensation for an amputee. As another example, the system 10 can be used in connection with an alternate reality or video game system that can be used by an ill individual or a healthy individual. In a further example, the system 10 can be used in connection with a neural prosthesis device to restore the function of sensation to a paralyzed individual. In another example, the system 10 can be used to transform data recorded in one modality, such as an imaging modality like ultrasound, into sensation.

The system 10 makes up for the deficiencies of artificial sensation provided by electrical stimulation of one or more sensory nerves (e.g., by a neural prosthesis), which can provide a degree of sensory perception. This electrical stimulation alone, however, cannot inform the subject as to the level of intensity of the sensation. However, the system 10 can provide a stimulus that informs the subject as to the level of intensity of the sensory stimulus perceived by the subject. The perceived level intensity can be a reflection of the magnitude of the sensory stimulus.

The system 10 can include one or more electrodes 12, a waveform generator 14 (or stimulator), and a controller 16. The controller 16 can configure an electrical signal for stimulation based on a predefined intensity of sensory perception during an action. Upon receiving the configuration from the controller 16, the waveform generator 14 can provide the stimulation signal configured according to instructions from the controller 16 to the one or more electrodes 12. The one or more electrodes 12 can apply the stimulation signal to the subject as the action is performed (either by the subject or on the subject).

The one or more electrodes 12, the waveform generator 14, and/or the controller 16 can be configured to communicate via one or more wired and/or wireless connections. In some instances, the one or more electrodes 12 and the waveform generator 14 can comprise a neural prosthesis device. The neural prosthesis device can deliver an electrical stimulation from the waveform generator 14 to a portion of the peripheral nervous system that includes a portion of the sensory nervous system through the one or more electrodes 12. The one or more electrodes 12 can be implantable and/or external (e.g., surface electrodes). Examples of internal electrodes can include one or more contacts of a multi-contact electrode, such as a spiral cuff electrode or flat interface neural electrode (FINE) cuff electrode, or one or more single-contact electrodes. An example of an external electrode can include a skin electrode. The waveform generator 14 can be configured independently of the one or more electrodes 12 for external or internal (e.g., the waveform generator 14 can be implantable) use.

Figure 2:
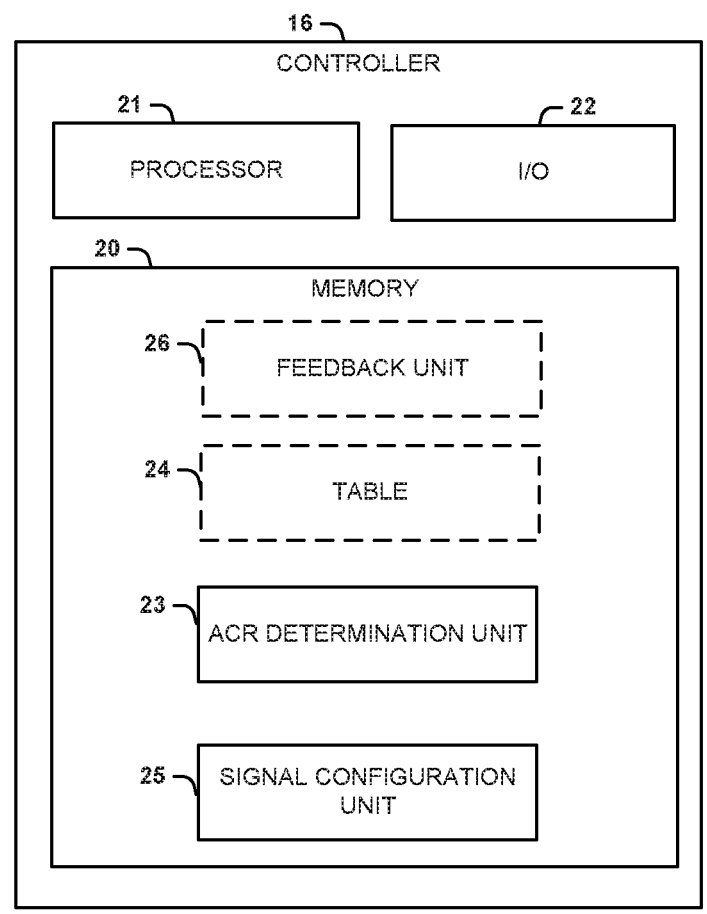
FIG. 2 is a block diagram illustration showing the controller of FIG. 1 in greater detail.

The controller 16, shown in more detail in FIG. 2, can include a non-transitory memory 20 and a one or more processors 21. In some instances, the non-transitory memory 20 and the one or more processors 21 can be hardware devices. Software aspects that can be implemented by the controller 16 can be stored as computer program instructions in the non-transitory memory 20. The non-transitory memory 20 can be any non-transitory medium that can contain or store the computer program instructions, including, but not limited to, a portable computer diskette; a random access memory; a read-only memory; an erasable programmable read-only memory (or Flash memory); and a portable compact disc read-only memory). The computer program instructions may be executed by the one or more processors 21. The one or more processors 21 can be one or more processors of a general-purpose computer, special purpose computer, and/or other programmable data processing apparatus. Upon execution of the computer program instructions, various functions/acts can be implemented by the controller 16 related to the configuration of the electrical stimulus signal that is sent to the waveform generator 14.

The controller 16 can configure parameters of the electrical signal, which can cause the subject to perceive a predefined level of intensity for a stimulation. Accordingly, the program instructions stored in the non-transitory memory 20 can include an ACR determination unit 23 and a signal configuration unit 25. The ACR determination unit 23 can configure the electrical stimulation signal with an activation charge rate (ACR) based on the predefined intensity of sensory perception by a subject during an action. The ACR is a single parameter of the electrical stimulation signal, which can be varied based on a desired level of perceived intensity to be perceived for a desired action. The ACR approximates the total spike rate evoked in the activated neural population and is directly proportional to the level of intensity perceived by the subject based on the stimulation. The ACR determination unit 23 combines the pulse frequency and the charge per pulse, which corresponds to the strength of the pulse (which depends on at least one of a pulse width value and a pulse amplitude value), to determine the ACR. Notably, the strength of pulses parameter and/or the frequency of pulses parameter in the stimulation signal can be altered throughout the stimulation as long as the ACR remains constant.

In some instances, the predefined level of intensity can be predefined based on a certain action. In some instances, the correlation between predefined level of intensity and the action can be stored in a table 24 that may be stored in the non-transitory memory 20 of the controller 16 and consulted by the ACR determination unit 23 upon configuring the electrical stimulation signal for the action. In other instances, the ACR can correspond to at least one of the predefined level of intensity for the action and/or the action stored in a table 24 that may be stored in the non-transitory memory 20 of the controller 16 and consulted by the ACR determination unit 23 upon configuring the electrical stimulation signal for the action.

The signal configuration unit 25 can configure the electrical stimulation signal with the ACR. For example, the signal configuration unit 25 can provide one or more parameters, including the ACR, to the waveform generator 14, which can generate the electrical stimulation signal with the ACR for application by the one or more electrodes 12. Upon application of the electrical stimulation signal, the subject perceives the desired level of intensity during the action. The perception of the level of intensity may be different from the actual predefined level of intensity, but is based on the predefined intensity of sensory perception. The signal configuration unit 25 can vary the strength of the pulses parameter and/or the frequency of the pulses parameter in the stimulation such that the ACR remains constant. For example, this alteration of the strength of the pulses parameter and/or the frequency of the pulses parameter can be used to combat adaptation or to control another aspect of the sensation, such as the location. The signal can be reconfigured with a new ACR based on a new action being performed by or on the subject.

The non-transitory memory can also store a feedback unit 26. The feedback unit 26 can receive feedback 18 and determine whether the level of intensity for the action is suffering from the effects of adaptation. The feedback 18, in some instances, can be provided by the subject related to adaptation as an open loop system. In other instances, the feedback 18 can be provided by the system 10 as a closed loop system, in which one or more sensors record a feature related to sensed intensity reflective of adaptation. In either case, the feedback unit 26 can account for the effects of adaptation on the ACR. Based on at least a portion of the feedback 18, the feedback unit 26 can signal the ACR determination unit 23 to determine a new ACR based on the adaptation. The signal configuration unit 25 can reconfigure the electrical stimulation signal with the new ACR (e.g., by controller 16). The reconfigured ACR can be based on adaptation exhibited in the feedback signal. The new electrical stimulation signal can induce the subject to perceive a new level of intensity during the action based on the reconfigured stimulation signal with the new ACR.

IV. Methods

Figure 3:
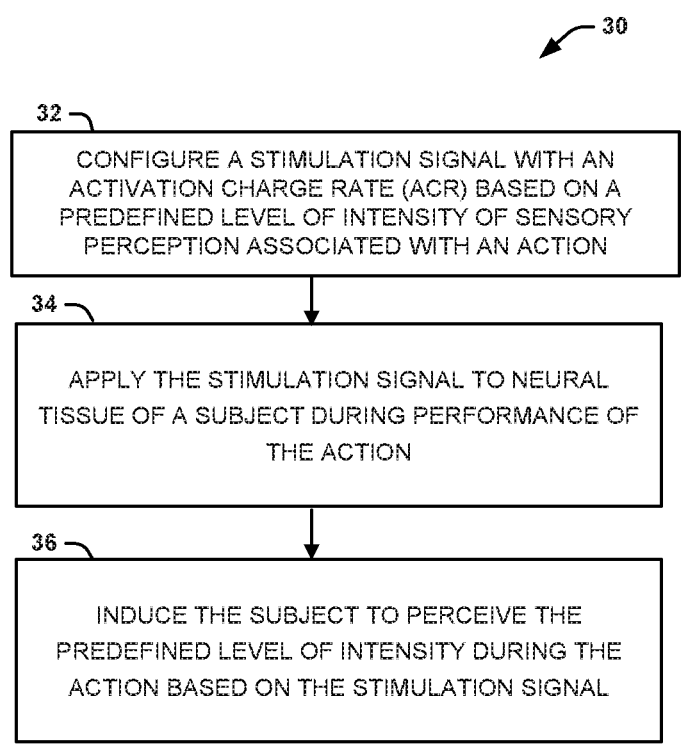
FIG. 3 is a process flow diagram of an example method for controlling levels of perceived intensity of a sensory stimulus in accordance with another aspect of the present disclosure.
Figure 4:
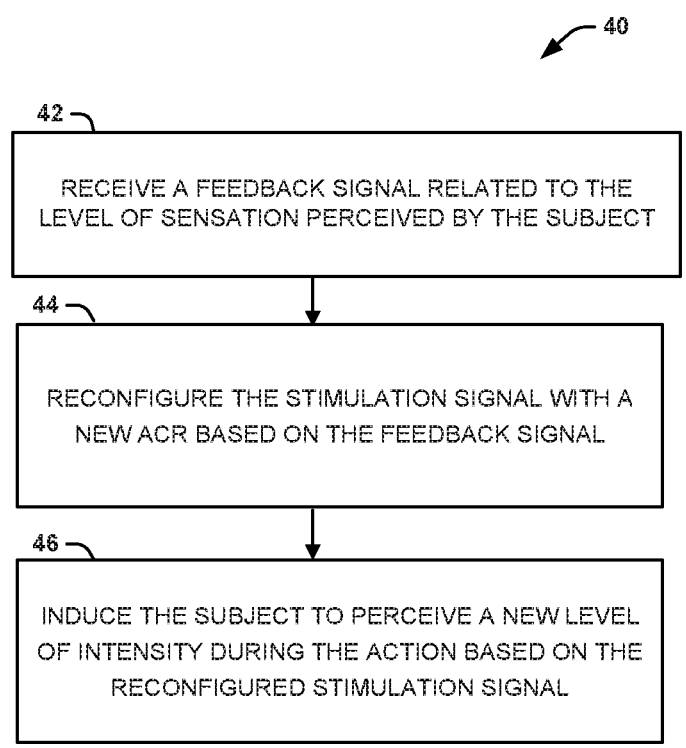
FIG. 4 is a process flow diagram of an example method for reconfiguring the stimulation of FIG. 3 to account for a change in perceived intensity.

Another aspect of the present disclosure can include methods for controlling the magnitude of a stimulation perceived by a user. FIG. 3 shows a method 30 for controlling levels of perceived intensity of a sensory stimulus. FIG. 4 shows a method 40 for reconfiguring the stimulation of FIG. 3 to account for a change in perceived intensity. The methods 30 and 40 can be executed by hardware—for example, at least a portion of the system 10 shown in FIG. 1. In each of the example methods, the levels of perceived intensity can be controlled and updated in real time. For example, the levels can be controlled based on an input from a sensor that senses the environment or the subject's body. Additionally, the levels can be controlled based on an image or input/feedback.

The methods 30 and 40 are illustrated as process flow diagrams with flowchart illustrations. For purposes of simplicity, the methods 30 and 40 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40. Additionally, one or more elements that implement the methods 30 and 40, such as controller 16 of FIG. 1, can include a non-transitory memory 20 and one or more processors 21.

Referring now to FIG. 3, illustrated is a method 30 for controlling levels of perceived intensity of a sensory stimulus. The levels of intensity perceived by a subject can be controlled based on the configuration of an electrical stimulation signal with a certain activation charge rate (ACR). In some instances, the ACR can be variable based on an input (e.g., from a sensor, based on a predefined program, or another type of input) The subject can be, for example, an able-bodied individual, an ill individual, an amputee, and/or a paralyzed individual.

At step 34, a stimulation signal can be configured (e.g., by controller 16) with an ACR that is set to an initial value based on a predefined intensity of sensory perception by a subject during an action. The ACR can be constant for a time period, which may be momentarily or indefinitely. In some instances, the ACR can be updated in real time to accommodate a charging input (e.g., from a sensor, from another type of input, etc.). The ACR is a single parameter of the stimulation signal that approximates the total spike rate evoked in the activated neural population and combines the pulse frequency and the charge per pulse, which corresponds to the strength of the pulse. In fact, the ACR is directly proportional to the level of intensity perceived by the subject based on the stimulation. By controlling the ACR of the stimulation signal, a desired level of perceived intensity can be perceived for a desired action. Notably, the strength of pulses parameter (which depends on at least one of a pulse width value and a pulse amplitude value) and/or the frequency of pulses parameter in the stimulation signal can be altered throughout the stimulation as long as the ACR remains constant.

In some instances, the level of intensity can be predefined based on a certain action. For example, a firm handshake can be set with a lower level of intensity than a bone-crushing grasp. In some instances, the correlation between predefined level of intensity and the action can be stored in a table that may be stored in a non-transitory memory and consulted by a component of the system executing the method 30 upon configuring the stimulation signal for the action. In other instances, the ACR can correspond to at least one of the predefined level of intensity for the action and/or the action stored in a table that may be stored in the non-transitory memory and consulted by a component by the system executing the method 30 upon configuring the stimulation signal.

During performance of the desired action, at step 34, the stimulation signal can be applied (e.g., by one or more electrodes 12 of a neural prosthesis device) to neural tissue. Based on application of the stimulation signal with the ACR set for the action, at step 36, the subject can be induced to perceive the predefined level of intensity of sensory perception. The predefined level of intensity of sensory perception can correspond to the magnitude of the sensation for the action.

In some instances, the level of intensity for the action can suffer from the effects of adaptation. As an example, the method 40 can account for the effects of adaptation on the ACR. At step 42, feedback related to the level of sensation perceived by the subject can be received (e.g., by controller 16). Based on at least a portion of the feedback, at step 44, the stimulation signal can be reconfigured with a new ACR (e.g., by controller 16). The reconfigured ACR can be based on adaptation exhibited in the feedback signal. At 46, the subject can be induced to perceive a new level of intensity during the action based on the reconfigured stimulation signal with the new ACR.

V. Experimental

The following example is shown for the purpose of illustration only and is not intended to limit the scope of the appended claims. This example shows how perception of a magnitude of sensation can be manipulated systematically by varying activation charge rate (ACR), a single stimulation quantity.

Materials and Methods

Study Design

The goal of this study was to determine how stimulation pulse width and pulse frequency impact the perceived intensity of artificial tactile percepts evoked through electrical stimulation. Tactile intensity was assessed in seven electrode contacts in two upper limb amputee volunteers in a series of forced-choice tasks for intensity discrimination, perceived magnitude rating, and artificial to natural sensation matching. The data were used to create a model of the neural basis of perceived intensity. All experiments were double-blinded with randomized stimulus presentation order. A computer program controlled stimulation and raw data was analyzed by custom programs.

Subject inclusion criteria included unilateral, upper limb amputees, age 21 or older, who are current users of a myoelectric prosthesis or prescribed to use one, and have viable target nerves in the residual limb. Potential subjects were excluded because of poor health (uncontrolled diabetes, chronic skin ulceration, history of uncontrolled infection, active infection) or the presence of significant, uncontrolled persistent pain in the residual or phantom limb.

Subjects

Two male unilateral right-arm trans-radial amputees were implanted with Flat Interface Nerve Electrodes (FINEs) or CWRU spiral cuffs around their median, ulnar, and radial nerves in their residual limbs. Briefly, subject 1 had a right trans-radial amputation just proximal to the wrist in 2010 due to a traumatic injury, and was implanted in May of 2012 with 8-contact FINEs around his right median and ulnar nerves and a 4-contact CWRU spiral cuff around his right radial nerve. Subject 2 had a right trans-radial amputation in 2004 due to a traumatic injury, and was implanted in January of 2013 with 8-contact FINEs around his median, ulnar, and radial nerves. The present study was carried out between months 32 and 40 post-implant for subject 1 and months 26 and 32 post-implant for subject 2. The subjects visited the lab for six-hour testing sessions every 2-6 weeks, depending on their availability. In referring to electrodes in the figures, the convention Ex.y, where x denotes the subject (1 or 2) and y denotes the electrode for that subject (ranging from 1 to 7), was used. All study devices and procedures were reviewed and governed by the US Food and Drug Administration (FDA) Investigational Device Exemption (IDE), Cleveland VA Medical Center Institutional Review Board, and the Dept. of the Navy Human Research Protection Program (DON HRPP). Informed consent was obtained from both subjects.

Peripheral Nerve Stimulation

Figure 5:
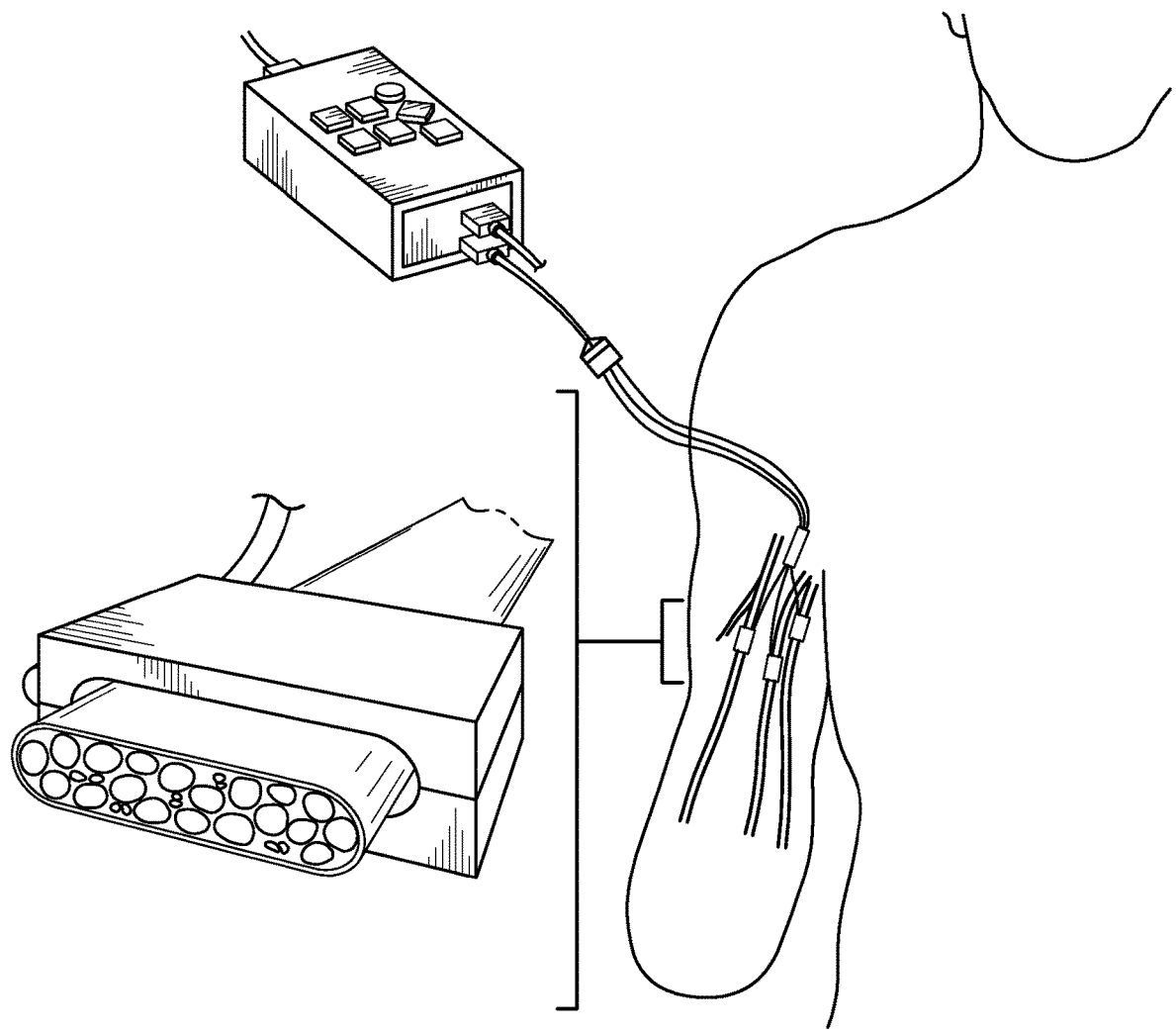
FIG. 5 is an illustration of an example system that delivers electrical stimulation to one or more of a subject's nerves.

All electrical stimuli consisted of trains of charge-balanced, square-wave, biphasic pulses with cathodal phase leading delivered by a custom Universal External Control Unit (UECU, Cleveland FES Center) stimulator to a single contact in the median nerve cuff (FIG. 5). The electrical returns consisted of 1 to 3 other contacts in the cuff such that stimulation elicited sensations on the palmar surface of the hand and did not interfere with the control of the myoelectric prosthesis. On each testing day, the subject's threshold on each cathodic contact was obtained using a two-alternative forced choice tracking paradigm in two stages, focusing on the long-pulse width (PW) portion of the strength-duration curve. In stage 1, the pulse amplitude (PA) threshold was found: On each trial, stimuli consisted of 5 s long pulse trains at a pulse frequency (PF) of 100 Hz and a PW of 255 μs, the largest PW achievable with the stimulator, and the subject reported if he perceived the stimulus. PA started at 0.3 mA and increased by 0.1 mA until the subject reported sensation. In stage 2, the PW threshold was found: PA was held at threshold, PW started at 130 μs, and on each trial, decreased by $130/2^n$ when the subject reported sensation or increased by $130/2^n$ when the subject did not, where n is the number of reversals. Threshold was assumed once the PW step size became less than 5 μs.

Once threshold was obtained, PW was increased in small steps to determine the range of parameters that led to sensations without causing discomfort. The midpoint of the range of PWs that elicited sensations was then selected as the set point PW for all subsequent discrimination trials. Similarly, stimuli at a range of PFs (at the set point PW) were presented to ensure that stimuli were perceptible and comfortable. The location, intensity, and quality of the sensations were recorded for several stimuli that spanned the range of PWs and PFs used in the discrimination experiments (described below). The quality of sensations tended to remain constant over the range of parameters tested.

Intensity Discrimination

Figure 6A:
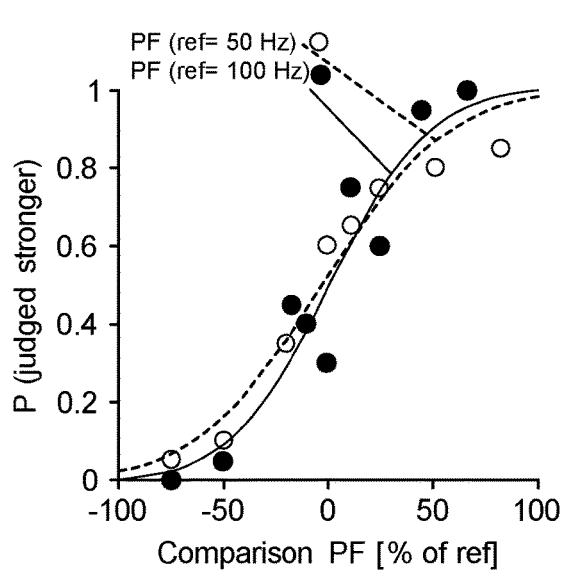
FIG. 6 includes plots showing a subject's ability to discriminate intensity, demonstrating that the relationship between pulse width (PW) and intensity is pulse frequency (PF)-dependent.
Figure 6B:
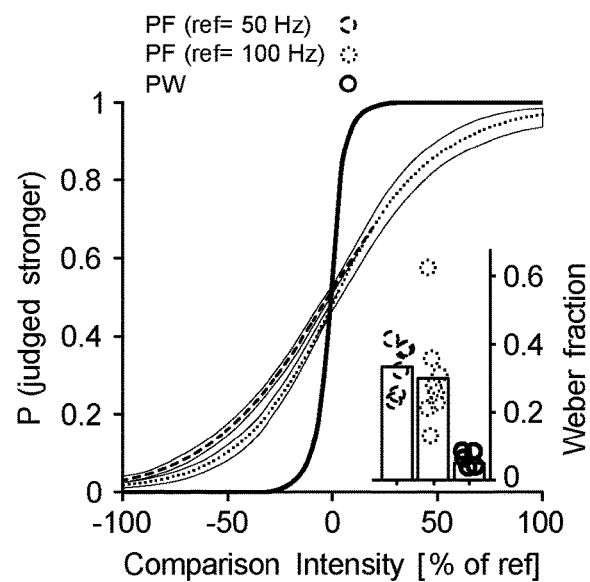
Figure 6C:
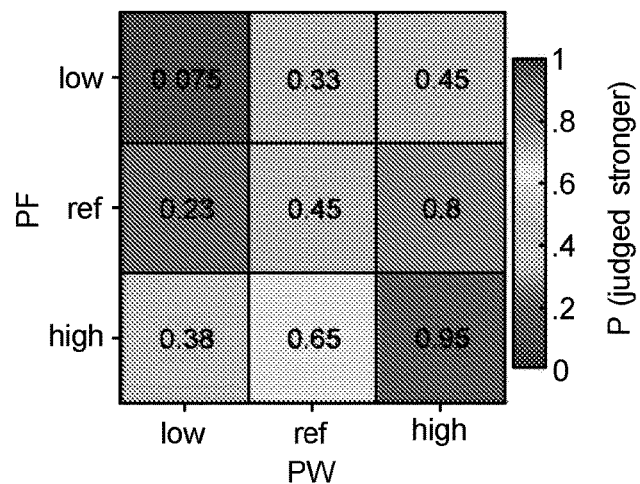
Figure 7A:
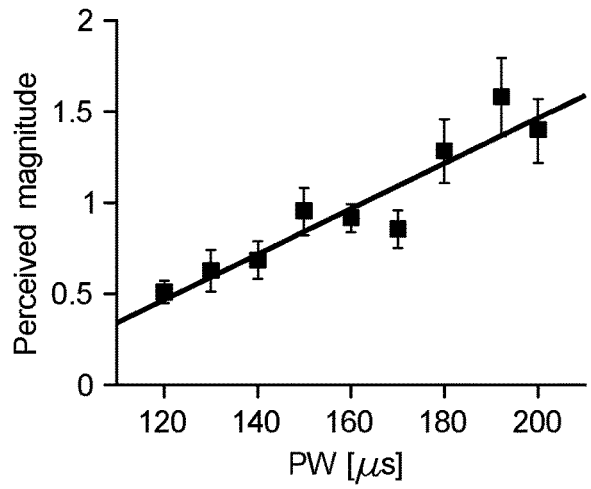
FIG. 7 includes plots showing scaling of perceived magnitude, demonstrating that the relationship between PW and intensity is PF-dependent.
Figure 7B:
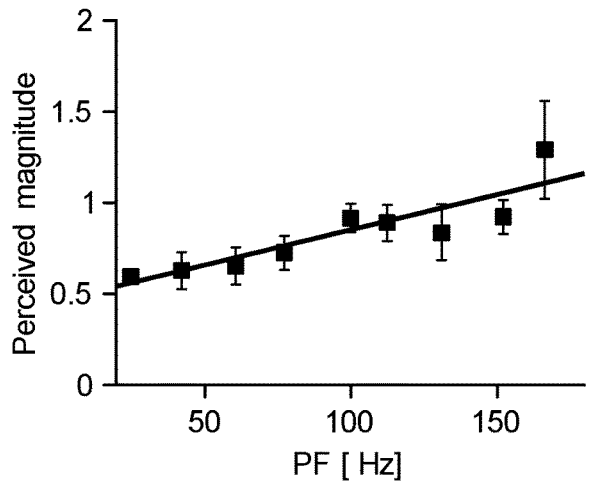
Figure 7C:
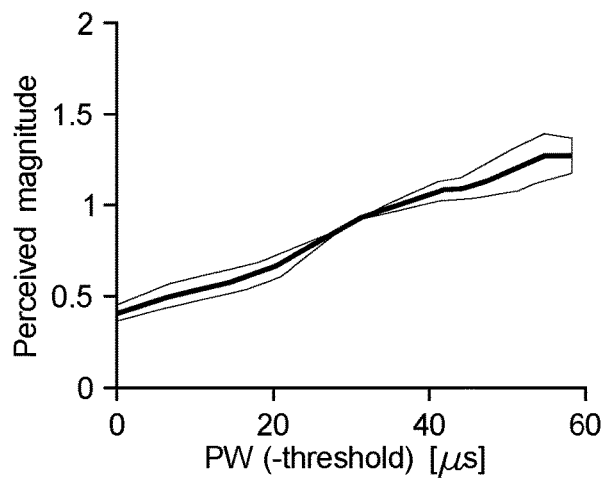
Figure 7D:
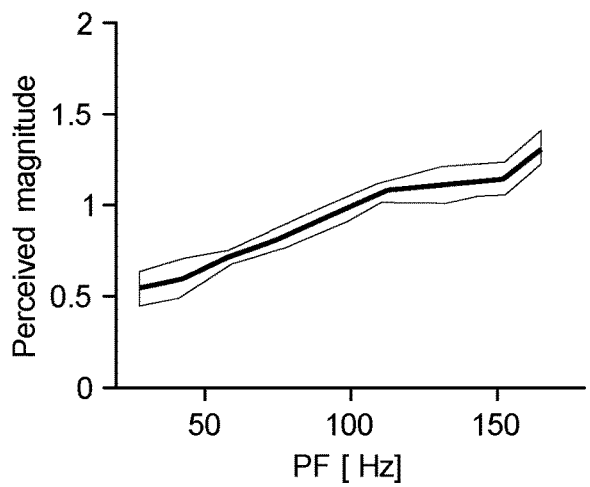
Figure 7E:
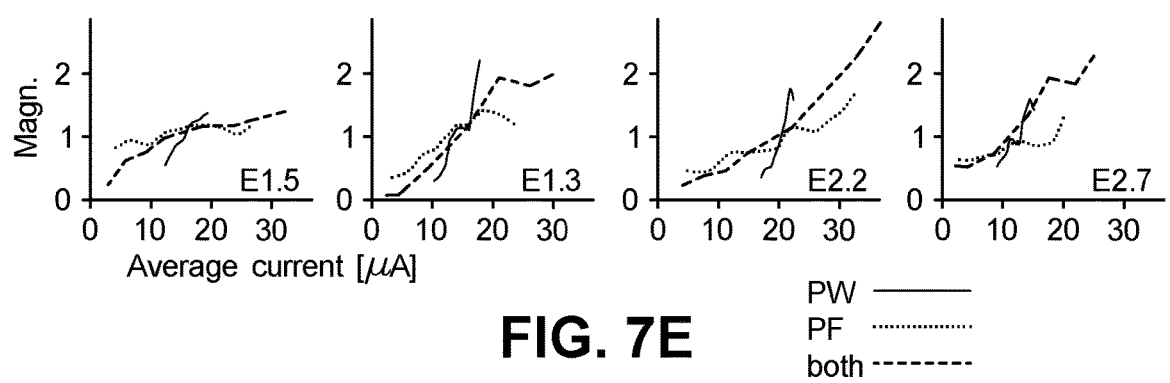
Figure 8A:
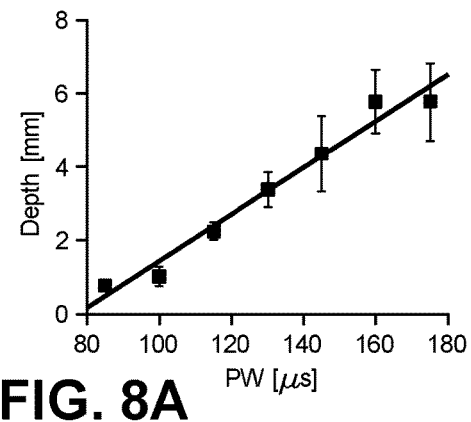
FIG. 8 includes plots showing the matching of fingertip indentations on a subject's residual limb to electrical stimuli delivered to the contralateral nerve, demonstrating that the relationship between PW and intensity is PF-dependent.
Figure 8B:
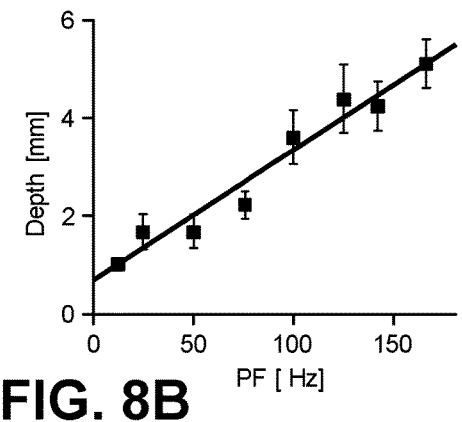
Figure 8C:
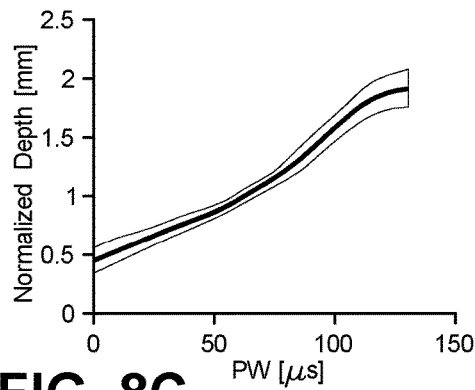
Figure 8D:
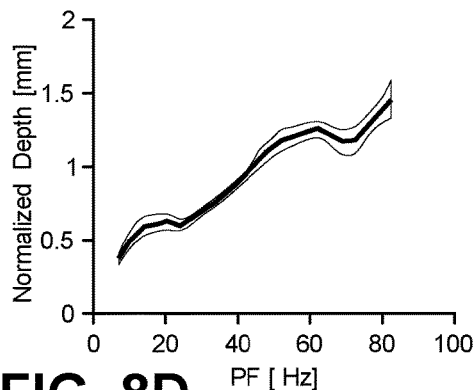
Figure 8E:
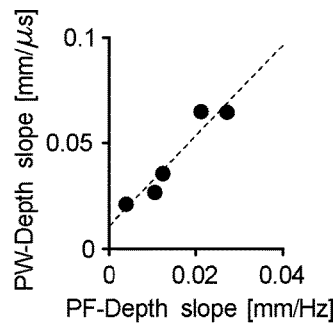
Figure 8F:
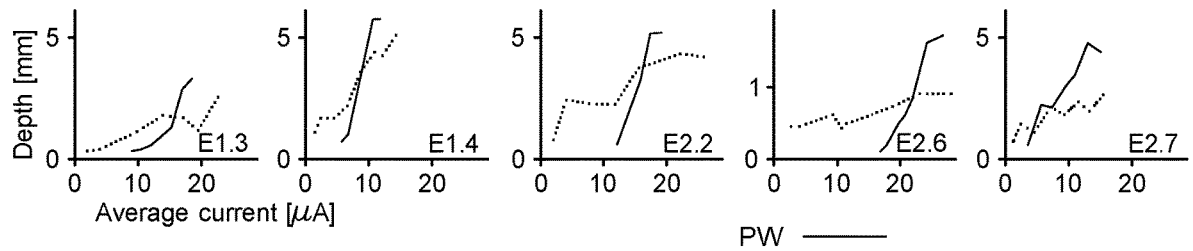

On each trial, two stimuli were presented, and the subject's task was to indicate which of the two stimuli was more intense (FIG. 6). Each experimental block comprised 180 trials and subjects were given a break between blocks. In each block, each stimulus pair was presented 20 times, and both the order of stimuli within the pair and the order of the pairs was varied pseudo-randomly. The two pulse trains lasted 1 s and were separated by a 1-s inter-stimulus interval. The subject was instructed to ignore any changes in quality, duration, or location of the sensations, if such changes were to occur, and to focus solely on the intensity or magnitude of the sensation. Both the subject and the experimenter were blinded to the particular stimulation conditions of each trial. Discrimination data were fit with cumulative normal distributions to obtain psychometric functions. The just noticeable difference (JND) was estimated as the change in the stimulation parameter (PF or PW) that yielded 75% correct performance. Each function yielded two estimates of the JND (one for decreases, the other for increases in that parameter relative to the reference parameter value), which were then averaged.

PF discrimination. Stimuli in each pair differed only in PF, with PA and PW held constant at their set point values, as described above. Each pair consisted of a stimulus at a reference PF and the other was at a test PF. Two reference PFs were tested—50 Hz and 100 Hz—and, for each reference, the test PFs ranged from 25 to 175% of the reference PF with the following caveat: because the stimulator could only produce frequencies that were integer millisecond divisions of one second (e.g., f=1/1 ms, ½ ms, ⅓ ms, etc), the nearest frequencies to achieve these reference percentages were used. Thus for the 100 Hz reference, the test stimuli were 25, 50, 83.3, 90.91, 100, 111.1, 125, 142.9, 166.7 Hz, and for the 50 Hz reference, the test stimuli were 12.5, 25, 40, 45.5, 50, 55.6, 62.5, 76.9, 90.9 Hz.

PW discrimination. Stimuli in each pair differed in PW, with PF held constant at 100 Hz and PA at its set value. One stimulus in each pair was the reference stimulus, where the PW was the set value used in the frequency discrimination trials. The other stimulus in the pair was the test stimulus, with PW typically ranging from 75 to 125% of the reference PW.

PF & PW discrimination. Stimuli in each pair differed in PW, PF, or both. One stimulus in the pair was always the reference stimulus, in which the PF and PW were at their set point values. This reference stimulus was compared to nine test stimuli, that included every possible permutation of PF, which took on one of three values (at the reference level, below it, or above it), paired with a PW, which also took on one of these three values. The high and low values were selected based on prior trials to be slightly greater than or less than one JND (estimated from the PF and PW discrimination functions), respectively. For example, the PFs for Subject 1 were 83.3, 100, and 125 Hz because the PF JND was found to be around 24 Hz on this contact, and the PWs were 121, 130, and 139 μs, because the PW JND was found to be around 10 μs on this contact.

Magnitude Estimation

During each trial, a 1 s-long pulse train was delivered and the subject's task was to state a number whose magnitude corresponded to the magnitude of the evoked sensation. If a stimulus was imperceptible, it was ascribed the number zero. If one stimulus felt twice as intense as another, it was given a number that was twice as large. Subjects were encouraged to use fractions and decimals as needed and there was not a maximum value. Trials were separated by at least 3 seconds to minimize adaptation. Subjects performed four experimental blocks, each consisting of 67 trials and separated by breaks. Ratings were normalized by dividing by the grand mean rating on their respective blocks. In some cases, only 3 blocks were run due to time constraints.

The following three conditions were intermixed in a pseudo-random order in each experimental block:

PF manipulation: The PW was constant at the reference PW and the PF varied over a range from 25 to 166 Hz to be consistent with the discrimination and matching experiments.

PW manipulation: PF was constant at 100 Hz and the PW varied along the perceptible and comfortable range.

PF and PW manipulation: The PF and PW spanned the same ranges as the PF and PW manipulations but increased together.

Electrical to Mechanical Intensity Matching

Indentation stimuli were applied with micron precision (±2 μm) using a stage driven by a MX80LP servo motor with a 0.5 μm encoder (Parker Hannifin Corp., Cleveland, Ohio). The motor was controlled by a ViX250-IH servo driver (Parker Hannifin Corp.) under computer control using custom software. The stage was mounted on a stable frame constructed from extruded aluminum rods. On each experimental block, the indenter was positioned over the (intact) left hand with the tactor centered on the location that matched the projected location of the sensations evoked when stimulating through the contact tested on that experimental block. The skin was pre-indented by ~500 μm to ensure that the tactor maintained contact with the skin over the entire block. Each trial consisted of a mechanical stimulus delivered to the intact hand paired with an electrical stimulus delivered through a given contact. The stimuli each last 1 s and were separated by a 1 s inter-stimulus interval, followed by a response interval. The order of presentation of the stimuli (electrical or mechanical first) was randomized. The subject indicated which stimulus (mechanical or electrical) felt stronger. Each experimental block was divided into sub-blocks during which the electrical stimulus remained constant. Within each sub-block, the depth of mechanical indentation increased (decreased) with a step size of 2 dB if the mechanical stimulus on the previous trial had been perceived as more (less) intense. In experiments with Subject 1, the step size decreased from 2 to 0.25 dB after the first reversal and the sub-block ended after the second reversal. In experiments with Subject 2, each sub-block ended as soon as the subject's response reversed. In all experiments, the starting indentation depth was randomly selected to span the range of achievable depths. Each electrical stimulus was presented in five sub-blocks; sub-blocks with different electrical stimuli were interleaved in pseudorandom order.

PF manipulation. Nine PFs were selected to span the range tested in the PF discrimination task (12-166 Hz).

PW manipulation: Seven PWs were selected to span a range that was both perceptible and comfortable.

Statistical Analysis

All data were reported as mean±standard deviation. Student's t-test with alpha=0.05 was used for comparisons between stimulation conditions.

Results

Intensity Discrimination

Subjects discriminated the perceived intensity of pairs of stimulation pulse trains that varied in pulse width (PW), pulse frequency (PF), or both. These experiments yielded psychometric functions relating discrimination performance to differences in stimulation intensity (PW, PF, or both). To the extent that small increments in either parameter are discriminable, a large number of intensity levels can be signaled to the subject via the neural interface.

Systematic changes in stimulation parameters yielded systematic changes in the perceived magnitude of the evoked percepts as evidenced by smooth psychometric functions, which are similar to those found in intact sensory systems (FIG. 6, element A). The just noticeable difference (JND) is defined as the change in a stimulation parameter that yields 75% correct discrimination. The JND for PF was 16.5±1.6 Hz (mean±sd) and 29.6±4.6 Hz at 50 and 100 Hz references, respectively. To compare discriminability across stimulation conditions, the Weber fraction, which is the JND divided by the reference was calculated. The Weber fractions obtained at the two reference frequencies were 0.33 and 0.30; these were statistically indistinguishable (unpaired t-test, p=0.61, FIG. 6, element B inset). The JND for PW was 6.7±1.0 μs, yielding a Weber fraction of 0.05, which was significantly lower than Weber fractions obtained with changes in PF (unpaired t-test, p<0.001 for both PF JNDs). Discriminability was higher when both PF and PW increased or decreased together than when either changed in isolation or when they changed in opposite directions (FIG. 6, element C). In other words, the relationship between PW and intensity is PF dependent.

Magnitude Estimation

Discrimination performance does not provide information about the range of elicited sensations. Indeed, all pulse trains might have elicited percepts whose magnitude was only slightly different, but reliably so. To achieve natural somatosensory feedback would require that the artificial sensation perceptions span a wide range of sensory magnitudes that matches the range experienced in every day life through an intact limb. To test the breadth of evoked sensations, subjects were asked to provide judgments of perceived intensity across the range of safe and comfortable stimulation parameters in a free magnitude scaling paradigm. As expected, the perceived intensity increased as PW (FIG. 7, elements A, C) and PF (FIG. 7, elements B, D) increased over the range of values tested. Importantly, perceived magnitudes of artificial touch spanned a wide range, increasing approximately ten-fold from the lowest to the highest intensity tested. To compare across stimulation parameters, the intensity was examined as a function of the average stimulation current, which is defined as the total stimulation charge applied per second (in units of μA):

$$I_{ave} = (PW*PA)*PF$$

The perceived magnitude as a function of average current was different depending on the mode of stimulation (t-test comparing regession slopes, all p<0.001, FIG. 7, element E): Slopes were steepest for PW, shallowest for PF, and intermediate for the combination of PF and PW.

Electrical to Mechanical Intensity Matching

Having established that varying pulse train parameters can elicit a large number of discriminable intensity percepts, and that these percepts span a wide range of intensities, it was sought to directly compare the magnitude of electrically evoked sensations to that of mechanically evoked ones. To this end, subjects were instructed to match mechanical skin indentations on their intact hand to electrical stimulation such that the sensory magnitude of the former matched that of the latter. This process was repeated for electrical stimuli that spanned the range of perceptible and comfortable PWs and PFs. It was found that PW and PF were approximately linear functions of indentation depth matched for perceived magnitude (FIG. 8, elements A-D). The slope of the functions obtained by varying PF and PW were consistent for each electrode contact but varied across contacts. Electrode contacts that yielded a high slope for indentation depth vs. PF also yielded a high slope for indentation depth vs. PW (FIG. 8, element E, r=0.96). The slopes of the functions were likely affected by several factors including the mechanical sensitivity at the location of the indentation, which probably varied across skin locations, and the electrical sensitivity of the stimulated fascicle, which varied according to its geometry and distance from the stimulating electrode. As was the case with the magnitude estimates, PW and PF had different effects on matched depths when stimulation was expressed in terms of the average stimulation current ($I_{ave}$) (t-test comparing regression slopes, all p<0.001).

The Neural Basis of Perceived Intensity

Increasing the PF of a stimulation results in an increase in the firing rate of activated neurons with minimal influence on the number of fibers activated, whereas increasing PW results in recruitment of additional neurons while minimally affecting the firing rate of the activated fibers since each pulse is too short to evoke multiple spikes in a given fiber. Importantly, electrical stimulation allows population size (via PW) and population firing rate (via PF) to be varied independently, which is not possible with natural stimulation as these two factors generally co-vary with mechanical stimulation of the skin.

Previous studies involving paired neurophysiological and psychophysical experiments yielded two theories of the neural basis of perceived intensity. According to the "hot zone" hypothesis, the perceived intensity is determined by the spike count across the population of afferent neurons whose receptive fields are directly under the stimulus, weighted by fiber type. According to the "population" hypothesis, the perceived intensity is determined by the spike count across the entire population of afferent neurons that is activated by the stimulus, again weighted by fiber type. These two hypotheses could not be disambiguated based on neurophysiological responses from the nerve and psychophysical ratings of perceived magnitude, as measured in monkeys and humans, respectively.

Results from the present study provide evidence against the hot zone model of perceived intensity. According to the hot zone model, increasing the PF of stimulation increases sensory magnitude by increasing the firing of neurons while minimally recruiting additional neurons. In contrast, increasing the PW recruits additional neurons while minimally affecting firing rate and has little impact on perceived intensity. On the other hand, the population model of perceived intensity predicts that increases in both stimulation parameters should affect perceived magnitude as they both modulate the total number of spikes elicited: one by increasing the spike rate of activated neurons, the other by recruiting more neurons. In other words, both temporal and spatial summation seem to play a role in shaping perceived intensity.

Figure 9:
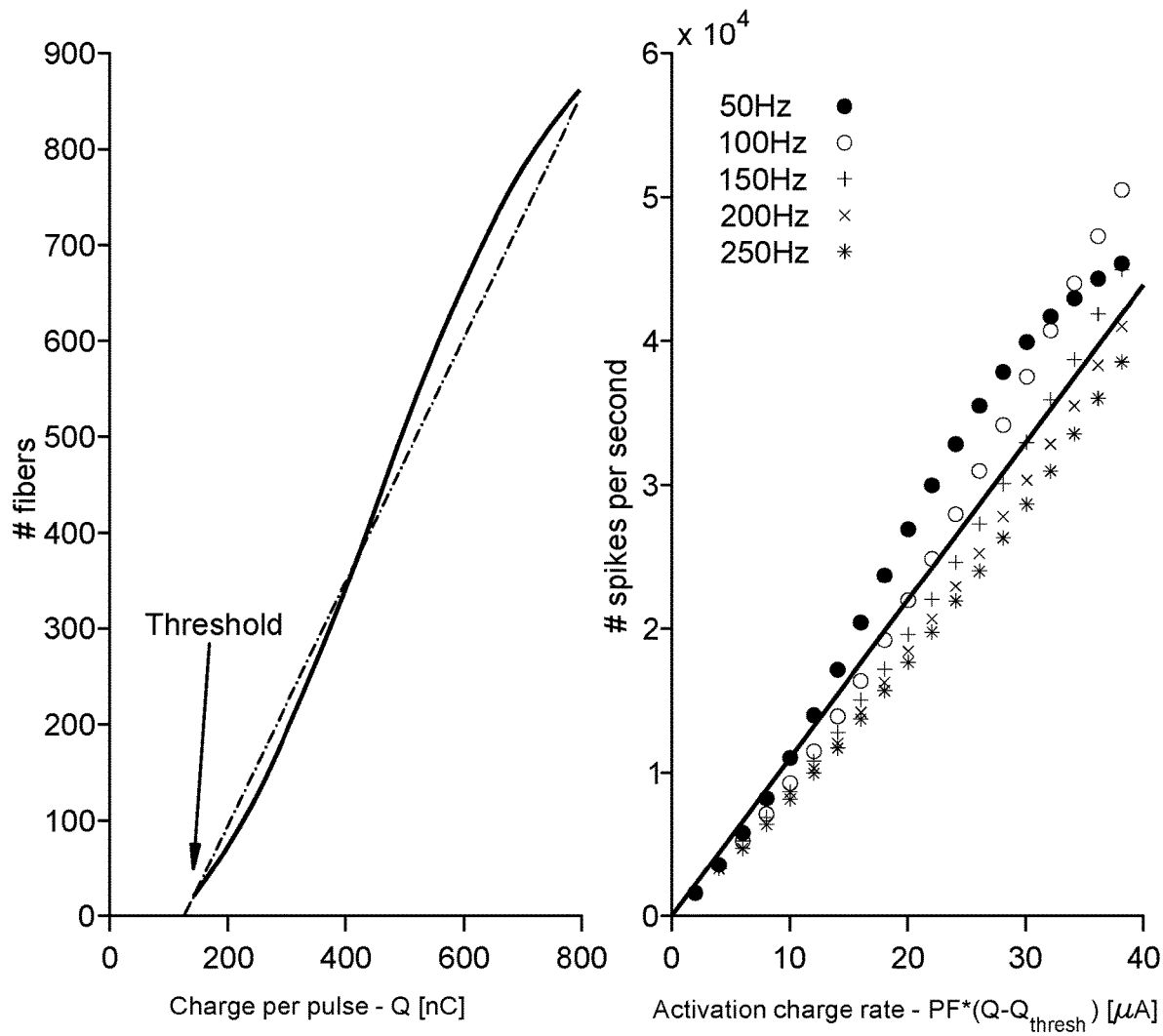
FIG. 9 includes plots illustrating the recruitment of fibers in a given fascicle.
Figure 10A:
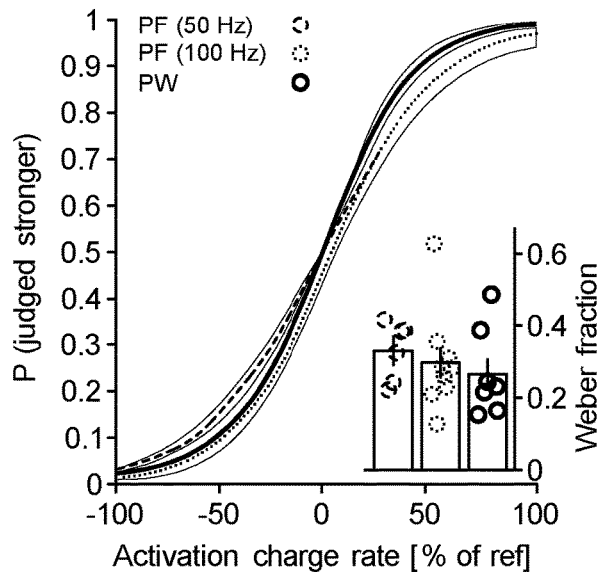
FIG. 10 includes plots showing that activation charge rate (ACR) determines perceived intensity for both PW and PF modulation.
Figure 10B:
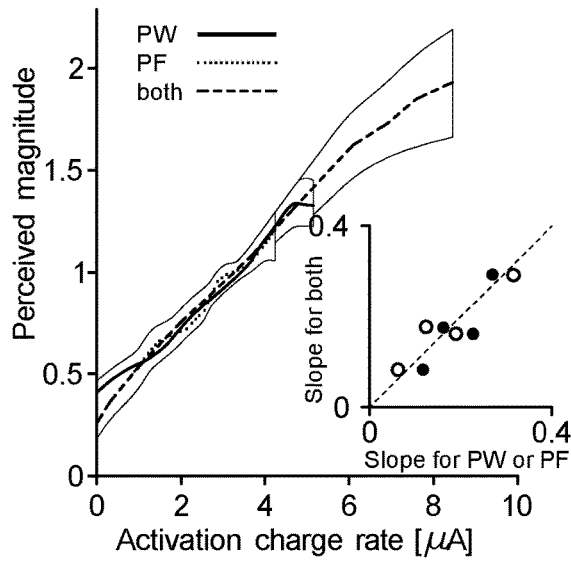
Figure 10C:
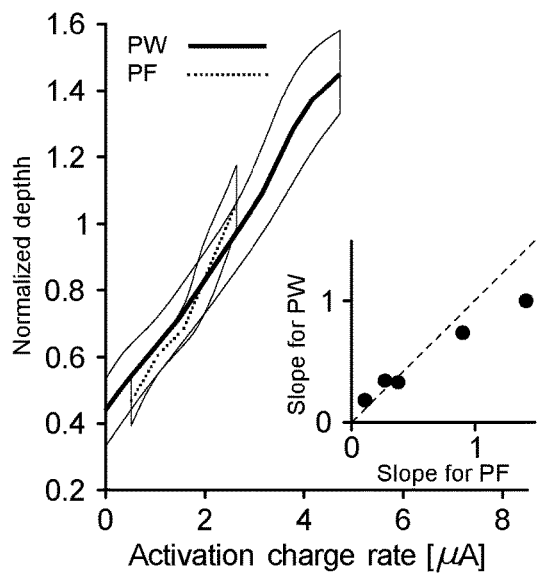
Figure 10D:
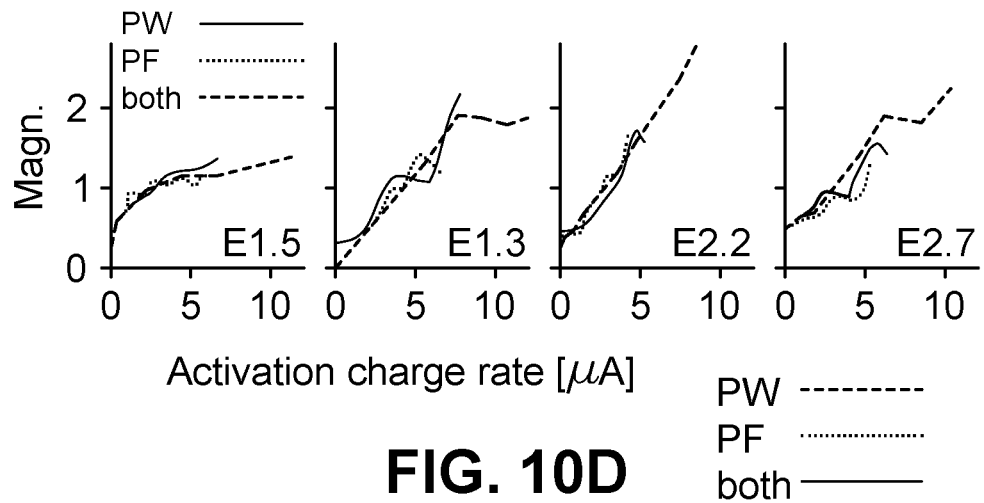
Figure 10E:
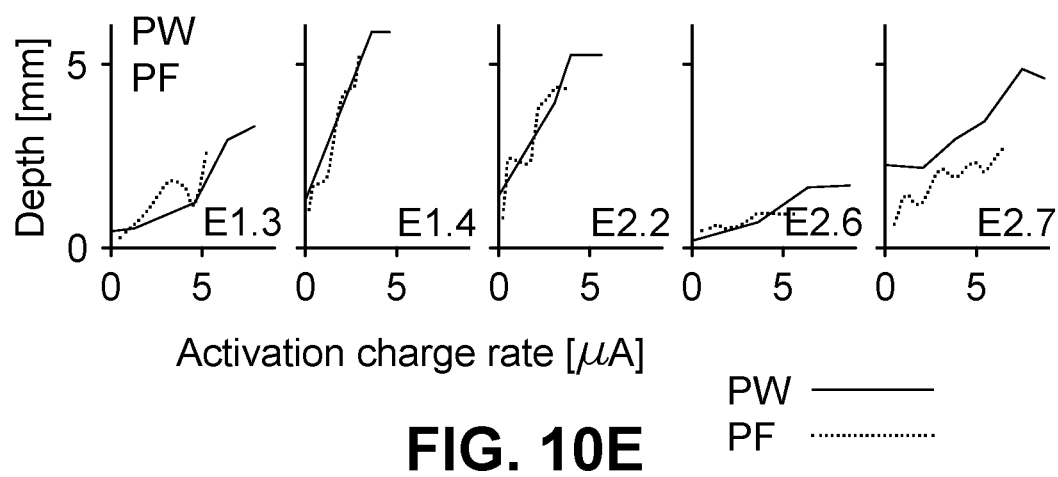

Based on the hypothesis that the population model could quantitatively account for the behavioral results, an expression to estimate how the population firing rate evoked by electrical stimulation varied as a function of PW and PF was derived. This model was predicated upon three assumptions: single fascicle activation, monotonic fiber recruitment, and single action potential per stimulation pulse. First, it was assumed that only one fascicle was activated by any given stimulus, an assumption that is supported by in vivo tests of FINEs in animals, and by the observation that, in these experiments, the spatial extent of the projected field was stable across stimulation parameters. Second, the number of fibers that were activated within the fascicle was a smooth, monotonic function of PW. This assumption is supported by the observation that perceived magnitude increased smoothly with increases in PW across the range tested. Recruitment—the proportion of fibers in the fascicle that are activated by each pulse—can be described as a sigmoidal function of PW (FIG. 9, element A). While the threshold and slope are expected to vary across electrodes—depending on the distance between the electrode and the stimulated fascicle, the precise electrical properties of the interposed tissue, the layout of surrounding fascicles, and the cross-sectional area of the fascicle, among others—a sigmoid is a generic description of the recruitment function. A detailed biophysical model of the human median nerve and of the effects of electrical stimulation on recruitment was implemented, showing that simulated recruitment curves were well approximated by a sigmoid function. When stimulation is above threshold and in the linear range of the sigmoid, the total number of fibers activated is well-approximated by a linear function of the total charge per pulse above threshold. Third, it was assumed that each pulse produced a single action potential in each activated fiber, given the short PWs (all ≤255 µs).

To estimate the total population spike rate, the proportion of activated fibers was multiplied by the stimulus frequency to yield a quantity dubbed activation charge rate (ACR):

$$ACR = (Q - Q_{threshold}) * PF$$

Since the stimulation pulses are square, the charge (Q) is the product of PA and PW and $Q_{threshold}$ is the charge at perception threshold. According to this model the population firing rate is approximately linear with ACR (FIG. 9, element B).

When the electrical stimuli were expressed in terms of ACR, and accounting for the effects of adaptation, the psychometric functions obtained in the discrimination experiment and resulting Weber fractions were consistent across the stimulation paradigms (FIG. 10, element A, t-test for each pair, p=0.61, 0.25 and 0.61, respectively). That is, the discriminability of two electrical stimuli could be predicted based on this metric regardless of which stimulation parameter was varied. Similarly, the magnitude scaling and indentation matching functions obtained when varying each of the two parameters (PW or PF) overlapped almost completely when expressed in terms of ACR (FIG. 10, elements B-C), and the slopes were highly consistent across tested conditions (FIG. 10, elements D-E, all p>0.05, except FIG. 10, element D leftmost panel p=0.0059). In other words, the perceived magnitude of any electrical stimulus could be predicted based on ACR regardless of the specific stimulation parameters. Given that ACR is a proxy for the evoked population firing rate, the present results are consistent with the hypothesis that the perceived magnitude of a tactile stimulus is determined by the total firing rate evoked in the population of mechanoreceptive afferents innervating the skin.

From the above description, those skilled in the art will perceive improvements, changes and modifications. Such improvements, changes and modifications are within the skill of one in the art and are intended to be covered by the appended claims.

The following is claimed:

1. A method comprising:
   configuring, by a system comprising a processor, a stimulation signal with an activation charge rate (ACR) set based on a predefined level of intensity to be perceived by a subject during an action, wherein the ACR comprises a strength of pulses parameter and a frequency of pulses parameter in the stimulation signal; and
   applying, by a neural prosthesis device coupled to the system, the stimulation signal to neural tissue of a subject during the action,
   wherein the subject is induced to perceive the predefined level of intensity during the action based on the stimulation signal; and
   altering, by the system, at least one of the strength of the pulses parameter and the frequency of the pulses parameter in the stimulation signal such that the ACR remains constant during the action,
   wherein the predefined level of intensity perceived by the subject remains constant while the at least one of the strength of the pulses parameter and the frequency of the pulses parameter in the stimulation signal is altered.

2. The method of claim 1, further comprising:
changing, by the system, the stimulation signal with a new ACR set based on an input from a sensor or a program;
updating, by the system, the stimulation signal with the new ACR; and
applying, by the neural prosthesis device coupled to the system, the updated stimulation signal to the neural tissue of the subject.

3. The method of claim 1, wherein the strength of the pulses parameter is based on at least one of a pulse width value and a pulse amplitude value.

4. The method of claim 1, wherein a level of sensory perception of the subject corresponds to a predefined level for the action based on the predefined level of intensity.

5. The method of claim 4, wherein the predefined level of intensity for the action is stored in a table that is consulted by the system upon configuring the stimulation signal for the action,
wherein the table is stored in a non-transitory memory of the system.

6. The method of claim 1, wherein the subject comprises at least one of an able-bodied individual, an ill individual, an amputee, and a paralyzed individual.

7. The method of claim 1, wherein the ACR is directly proportional to the predefined level of intensity perceived by the subject.

8. The method of claim 1, wherein a value of the ACR is stored in a table corresponding to the at least one of the predefined level of intensity and the action,
wherein the table is stored in a non-transitory memory of the system.

9. The method of claim 8, further comprising consulting, by the system, the table to determine the ACR associated with the action.

10. The method of claim 1, wherein the ACR is further based on feedback related to an effect of adaptation of the subject to the stimulation signal.

11. A system comprising:
at least one electrode;
a controller comprising a processor to configure a stimulation signal with an activation charge rate (ACR) based on a predefined level of intensity of sensory perception by a subject during an action,
wherein the ACR comprises a strength of pulses parameter and a frequency of pulses parameter in the stimulation signal,
wherein the strength of the pulses parameter and the frequency of the pulses parameter in the stimulation signal are variable such that the ACR remains constant during the action, and
wherein the ACR is set according to a desired level of sensation to perceived during the action based on the stimulation signal and the predefined level of sensory perception;
a waveform generator to generate the stimulation signal and provide the stimulation signal to the at least one electrode for application to the subject as an action is performed,
wherein the at least one electrode is configured to apply the stimulation signal to the subject as the action is performed.

12. The system of claim 11, wherein the strength of pulses parameter is based on at least one of a pulse width value and a pulse amplitude value.

13. The system of claim 11, wherein the controller configures the stimulation signal with a different ACR based on an input from a sensor.

14. The system of claim 11, wherein the predefined level of intensity is retrieved from a table stored in a non-transitory memory associated with the controller based on the action.

15. The system of claim 11, wherein the at least one electrode is an implantable electrode or an external electrode.

16. The system of claim 11, wherein the at least one electrode comprises at least one of a flat interface nerve electrode (FINE) or a spiral cuff electrode.

17. The system of claim 11, wherein the controller receives a feedback signal related to an effect of adaptation of the subject to the stimulation signal and determines the ACR further based on the feedback signal.

* * * * *